United States Patent
Wang

(10) Patent No.: US 9,259,594 B2
(45) Date of Patent: Feb. 16, 2016

(54) APPARATUS AND METHODS FOR DEEP TISSUE LASER THERAPY

(75) Inventor: Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 1157 days.

(21) Appl. No.: 13/274,378

(22) Filed: Oct. 17, 2011

(65) Prior Publication Data

US 2012/0095533 A1     Apr. 19, 2012

Related U.S. Application Data

(60) Provisional application No. 61/394,172, filed on Oct. 18, 2010, provisional application No. 61/471,743, filed on Apr. 5, 2011.

(51) Int. Cl.
*A61N 5/06* (2006.01)
*A61N 5/067* (2006.01)

(52) U.S. Cl.
CPC ......... *A61N 5/0613* (2013.01); *A61N 2005/063* (2013.01); *A61N 2005/067* (2013.01); *A61N 2005/0643* (2013.01)

(58) Field of Classification Search
None
See application file for complete search history.

(56) References Cited

U.S. PATENT DOCUMENTS

| | | | |
|---|---|---|---|
| 4,836,203 A | 6/1989 | Muller et al. | |
| 5,464,436 A | 11/1995 | Smith | |
| 7,245,369 B2 | 7/2007 | Wang et al. | |
| 7,545,493 B2 | 6/2009 | Wang et al. | |
| 2007/0043341 A1* | 2/2007 | Anderson | A61B 5/0059 606/12 |
| 2008/0170218 A1* | 7/2008 | Dantus | G01N 21/65 356/39 |
| 2008/0255638 A1* | 10/2008 | Wang | A61B 18/20 607/89 |
| 2010/0177376 A1* | 7/2010 | Arnold | G02B 3/00867 359/307 |
| 2011/0100880 A1* | 5/2011 | Recami | A61M 37/0092 209/1 |

* cited by examiner

*Primary Examiner* — Brian T Gedeon
*Assistant Examiner* — Ankit Tejani

(57) ABSTRACT

An improved apparatus and method for deep tissue laser therapy, in which the phase of the laser light is spatially modulated to produce a modulated laser beam. The modulated laser beam is able to restore its intensity profile even after being scattered by the skin or the superficial layer of the tissue, allowing it to penetrate deep into the tissue to provide efficient therapeutic treatment.

14 Claims, 2 Drawing Sheets

APPARATUS AND METHODS FOR DEEP TISSUE LASER THERAPY

REFERENCE TO RELATED APPLICATION

This application claims inventions which were disclosed in Provisional Patent Application No. 61/394,172, filed Oct. 18, 2010, entitled "APPARATUS AND METHODS FOR DEEP TISSUE LASER THERAPY", and 61/471,743, filed Apr. 5, 2011, entitled "APPARATUS AND METHODS FOR DEEP TISSUE LASER THERAPY". The benefit under 35 USC §119(e) of the above mentioned United States Provisional Applications is hereby claimed, and the aforementioned applications are hereby incorporated herein by reference.

FIELD OF THE INVENTION

This invention generally relates to laser therapy, and more specifically to apparatus and methods for deep tissue laser therapy.

BACKGROUND

Laser therapy is a medical and veterinary technique which uses laser light to stimulate or inhibit cellular function. Recently, this technique has been widely used for treating soft tissue injury, chronic pain, and promoting wound healing for both human and animal targets. The effectiveness of laser therapy is affected by a plurality of factors determined by the properties of the laser light source, e.g. wavelength, power density, energy fluence (dose), pulsing parameters (peak power, repetition rate, duty cycle), as well as by the physical characteristics of the patients, e.g. body-build, weight, gender, skin color, hair color, and body part to be treated, which in turn affects the absorption/scattering coefficient and penetration depth of the laser light in the biological tissue.

Biological tissues are heterogeneous structures, which have spatial variations in their optical properties. The spatial variation and density of these fluctuations make the biological tissue a highly scattering optical medium. A significant fraction of the laser light is scattered multiple times in the tissue, resulting in a low penetration depth. The low penetration depth makes existing laser therapy apparatus extremely inefficient in treating tissues deep below the skin. One way to reach those deep tissues is to increase the power density of the laser light. However, the high laser power may cause overheating and damage the skin tissue (or other superficial tissues). Another approach is to select a longer laser wavelength which is less scattered. However, the laser wavelength that provides the deepest penetration depth may not be the optimum wavelength that produces the best therapeutic effect.

There thus exists a need for an improved laser therapy apparatus and method, which is capable of delivering laser light to tissues deep below the skin for effective therapeutic treatment.

SUMMARY OF THE INVENTION

It is thus the goal of the present invention to provide an improved apparatus and method for deep tissue laser therapy, in which the phase of the laser light is spatially modulated to produce a modulated laser beam. The modulated laser beam is able to restore its intensity profile even after being scattered by the skin or the superficial layer of the tissue, allowing it to penetrate deep into the tissue to provide efficient therapeutic treatment.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
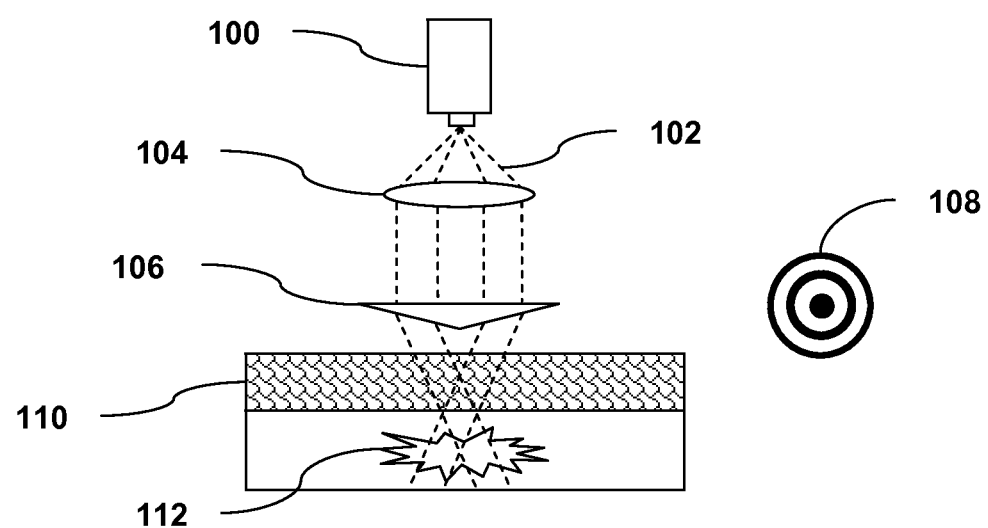
FIG. 1 illustrates a first exemplary laser therapy apparatus, which utilizes a 'non-diffracting' laser beam to provide therapeutic treatment to deep tissues.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to deep tissue laser therapy. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

A first exemplary embodiment of the laser therapy apparatus is shown in FIG. 1. The laser therapy apparatus comprises a laser light source 100, which preferably consists of solid state lasers or diode lasers. The diode lasers can be broad-stripe or broad-area semiconductor lasers for increased output power. An external or internal grating element can be integrated onto the diode laser to increase its coherence length, hence improving the laser beam's spatial homogeneity and spatial brightness (defined as the intensity of the laser beam divided by its divergence angle). Some examples of the grating stabilized diode laser can be found in U.S. Pat. Nos. 7,245,369 and 7,545,493, which are hereby incorporated herein by reference. The laser light 102 produced by the laser light source 100 is first collimated by an optical lens 104. The phase of the collimated laser beam is then spatially modulated by an axicon lens 106. This spatial phase modulation converts the laser beam from a Gaussian beam into a Bessel beam, which has a ring shaped intensity profile 108. The Bessel beam is a 'non-diffracting' beam having the capability of self-healing or self-reconstruction, i.e. the light beam can recover its initial intensity profile through constructive interference after being scattered or obscured by obstacles.

This capability allows the laser beam to penetrate through the highly scattering skin tissue 110 to provide therapeutic treatment to the subject biological tissue 112, which lies deep below the skin. The penetration depth of the Bessel beam can be controlled by controlling the waist diameter of the collimated laser beam as well as by controlling the cone angle of the axicon lens. The increased coherence length of the grating stabilized laser help to enhance the self-healing capability of the Bessel beam. The optical lens 104 and the axicon lens 106 can be integrated into a handpiece (not shown) for delivering the 'non-diffracting' Bessel beam into the biological tissue to be treated.

The laser light produces photochemical reaction in the subject biological tissue, e.g. up-regulation and down-regulation of adenosine triphosphate (ATP), reactive oxygen species, and nitric oxide. The photochemical reaction in turn produces the following therapeutic effects: (i) stimulating white blood cell activity; (ii) accelerating macrophage activity, growth factor secretion and collagen synthesis; (iii) promoting revascularization and micro-circulation; (iv) increasing fibroblast numbers and collagen production; (v) accelerating epithelial cell regeneration and speeding up wound healing; (vi) increasing growth-phase-specific DNA synthesis; (vii) stimulating higher activity in cell proliferation and differentiation; (viii) increasing the intra and inter-molecular hydrogen bonding.

The laser light source 100 may comprise multiple lasers with different output wavelengths, each matching with the absorption band of certain type of chromophores in the biological tissue. For example, the 810 nm laser light is well absorbed by the hemoglobin and melanin content of the tissue, while the 980 nm laser light is efficiently absorbed by the water content. The lasers may operate in a pulsed mode such that a high peak power is produced to further increase the penetration depth of the laser light and/or to trigger nonlinear photochemical reactions yet the average power of the laser light is maintained at low levels to avoid any tissue damage.

In a slight variation of the present embodiment, other methods may be used to produce the Bessel beam. For example, a tunable acoustic gradient index of refraction (TAG) lens may be utilized to produce the appropriate spatial phase modulation. The TAG lens consists of a cylindrical piezoelectric shell driven at ultrasonic frequencies to generate acoustic waves in a transparent filling fluid (e.g. silicone oil). The acoustic wave induces an alteration of the refractive index inside the lens, which in turn produces a spatial phase modulation onto the wavefront of the laser beam. In this approach, the penetration depth of the Bessel beam can be easily tuned by adjusting the frequency and amplitude of the acoustic wave. In addition to the Bessel beam, other types of 'non-diffracting' beams (e.g. Mathieu beams) may be utilized to improve the penetration depth of the laser light.

Figure 2:
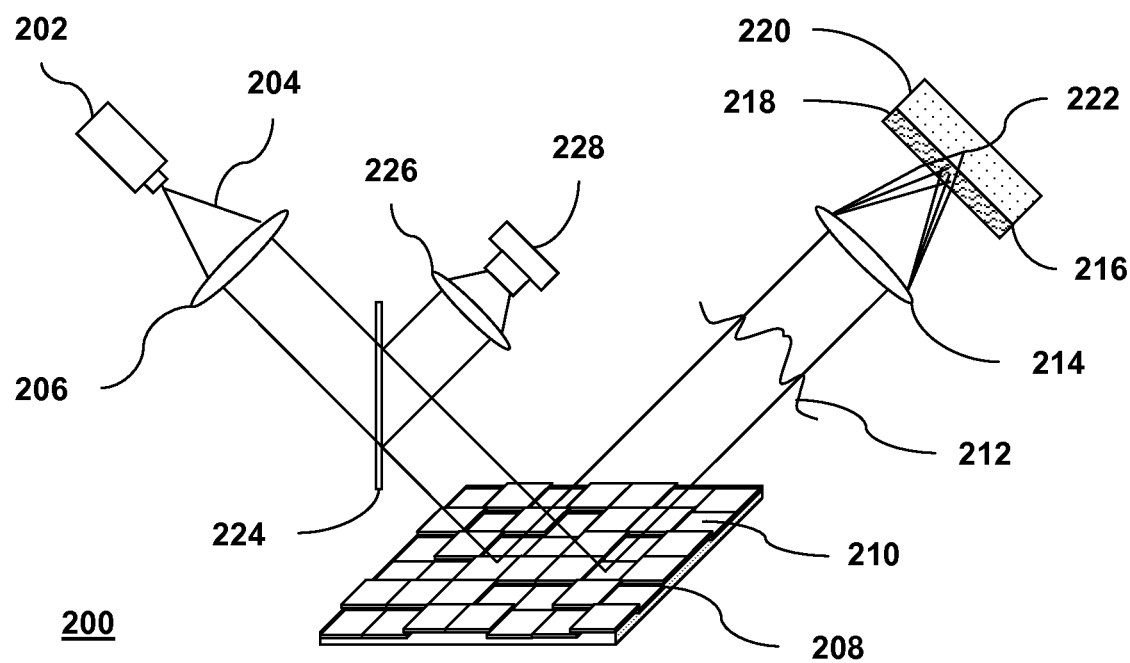
FIG. 2 illustrates a second exemplary laser therapy apparatus, which utilizes a spatially modulated laser beam to provide therapeutic treatment to deep tissues.

A second exemplary embodiment of the laser therapy apparatus is shown in FIG. 2. The laser therapy apparatus 200 comprises a laser light source 202. The laser light 204 produced by the laser light source 202 is first collimated by an optical lens 206. The phase of the collimated laser beam is then spatially modulated by a spatial light modulator (SLM) 208, which can be a liquid crystal based spatial light modulator or a MEMS (Micro-Electro-Mechanical Systems) based spatial light modulator. The spatial light modulator 208 comprises a plurality of individually controllable pixels 210, each pixel controlling the phase of a segment of the laser beam, thus producing a spatial phase modulation 212 onto the wavefront of the laser beam. The modulated laser beam passes through a second optical lens 214 to be focused into the subject biological tissue 216. The strong scattering of the superficial layer 218 of the subject tissue randomly changes the direction of the laser light and produces a disordered phase modulation. This disordered phase modulation is compensated by the phase modulation provided by the spatial light modulator 208, allowing the laser light to interfere constructively inside the tissue 216, thus creating a focus point 222 in the inner layer 220 of the subject tissue. The constructive interference overcomes the scattering loss of the tissue and greatly increases the power density of the laser light at the focus point 222. By scanning the laser beam and adjusting the spatial light modulator simultaneously, the practitioner can perform effective therapeutic treatment in any position and depth of the subject tissue. The increased coherence length of the grating stabilized laser help to enhance the constructive interference of the laser beam.

Referring to FIG. 2, focusing of the laser beam can be automatically fulfilled through feedback control provided by an imaging sensor 228. Here the reflected laser light from the tissue 216 is collected by the optical lens 214 and follows the opposite optical path to be modulated by the spatial light modulator 208. In a similar way as described above, any disordered phase modulation induced by random scattering of the tissue is compensated by the phase modulation provided by the spatial light modulator. The reflected laser light is then sampled by a beam splitter 224 and focused by a third optical lens 226 onto the imaging sensor 228. When the laser light is focused to a point 222 inside the subject tissue, a clear image of the focus point 222 is formed on the imaging sensor 228. By adjusting the spatial light modulator 208 and the optical lens 214 and in the meantime monitoring the image on the imaging sensor 228, the practitioner can precisely control the location and depth of the tissue to be treated. The laser light source 202, the spatial light modulator 208, the imaging sensor 228, and the related optical components can be integrated into a handpiece (not shown) for delivering the laser light into the subject biological tissue.

In a slight variation of the present embodiment, the structural information of the biological tissue is first obtained from known anatomy models or measured through an imaging means, such as computed tomography (CT), fluoroscopy, magnetic resonance imaging (MRI), radioisotope imaging, ultrasound imaging, x-ray radiography, millimeter-wave imaging, and optical tomography, which can 'see' through the surface layer of the biological tissue. The obtained structural information is utilized to estimate the phase modulation induced by scattering of the tissue. The spatial light modulator is then adjusted accordingly to compensate this scattering induced phase modulation and makes the laser light interfere constructively to produce a focus point inside the biological tissue.

In addition to laser therapy, the above disclosed technique can be used in other fields as well. One example is photodynamic therapy (PDT), where the laser light is focused to a point inside the biological tissue to activate a photosensitizer and produce singlet oxygen to selectively kill tumor cells. Another example is non-invasive laser surgery, where the laser light is focused to a point inside the biological tissue to selectively ablate a target tissue yet not cause any damage to the surrounding tissues.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A laser therapy apparatus for performing therapeutic treatment inside a biological tissue, the laser therapy apparatus comprising:
a laser light source for producing a laser beam;
an optical component for spatially modulating a phase of said laser beam to convert said laser beam into a Bessel beam; and
means for delivering said Bessel beam into the biological tissue for performing therapeutic treatment inside the biological tissue.

2. The laser therapy apparatus of claim 1, wherein said laser light source comprises a solid state laser.

3. The laser therapy apparatus of claim 1, wherein said laser light source comprises a diode laser.

4. The laser therapy apparatus of claim 3, wherein said diode laser comprises a grating stabilized broad-stripe or broad-area diode laser.

5. The laser therapy apparatus of claim 1, wherein said optical component comprises an axicon lens.

6. The laser therapy apparatus of claim 1, wherein said optical component comprises a tunable acoustic gradient index of refraction (TAG) lens.

7. A method for performing therapeutic treatment inside a biological tissue, the method comprising the steps of: providing a laser light source for producing a laser beam; providing a spatial light modulator for spatially modulating a phase of said laser beam to produce modulated laser beam; and delivering said modulated laser beam into the biological tissue; wherein said spatial light modulator is configured to cause said modulated laser beam to interfere constructively to produce a focus point inside the biological tissue for performing therapeutic treatment.

8. A laser therapy apparatus for performing therapeutic treatment inside a biological tissue, the laser therapy apparatus comprising: a laser light source for producing a laser beam; a spatial light modulator for spatially modulating a phase of said laser beam to produce a modulated laser beam; and means for delivering said modulated laser beam into the biological tissue; wherein said spatial light modulator is configured to cause said modulated laser beam to interfere constructively to produce a focus point inside the biological tissue for performing therapeutic treatment.

9. The laser therapy apparatus of claim 8, wherein said spatial light modulator comprises a liquid crystal based spatial light modulator.

10. The laser therapy apparatus of claim 8, wherein said spatial light modulator comprises a MEMS (Micro-Electro-Mechanical Systems) based spatial light modulator.

11. The laser therapy apparatus of claim 8, further comprising an imaging sensor for monitoring the biological tissue and providing feedback control to said spatial light modulator for automatically controlling said focus point inside the biological tissue.

12. The laser therapy apparatus of claim 8, wherein said laser light source comprises a solid state laser.

13. The laser therapy apparatus of claim 8, wherein said laser light source comprises a diode laser.

14. The laser therapy apparatus of claim 13, wherein said diode laser comprises a grating stabilized broad-stripe or broad-area diode laser.

* * * * *